United States Patent
Rebière

(10) Patent No.: US 9,534,028 B2
(45) Date of Patent: Jan. 3, 2017

(54) METHOD FOR THE PREPARATION OF A SERUM PROTEIN CONCENTRATE

(71) Applicant: LB LYOPHARM S.R.L., Bolzano (IT)

(72) Inventor: Christian Rebière, Merano (IT)

(73) Assignee: LB LYOPHARM S.R.L., Bolzano (IT)

( * ) Notice: Subject to any disclaimer, the term of this patent is extended or adjusted under 35 U.S.C. 154(b) by 0 days.

(21) Appl. No.: 14/421,671

(22) PCT Filed: Aug. 13, 2013

(86) PCT No.: PCT/IB2013/056610
§ 371 (c)(1),
(2) Date: Feb. 13, 2015

(87) PCT Pub. No.: WO2014/027305
PCT Pub. Date: Feb. 20, 2014

(65) Prior Publication Data
US 2015/0203552 A1    Jul. 23, 2015

(30) Foreign Application Priority Data

Aug. 13, 2012   (IT) .............................. RM2012A0412

(51) Int. Cl.
| | |
|---|---|
| *A23C 9/12* | (2006.01) |
| *C07K 14/47* | (2006.01) |
| *A23J 1/20* | (2006.01) |
| *A23J 3/08* | (2006.01) |
| *A23C 9/142* | (2006.01) |
| *A23C 9/13* | (2006.01) |
| *A23C 21/00* | (2006.01) |
| *A23L 2/66* | (2006.01) |
| *A61Q 19/00* | (2006.01) |
| *A61K 8/98* | (2006.01) |
| *C07K 1/36* | (2006.01) |

(52) U.S. Cl.
CPC .............. *C07K 14/47* (2013.01); *A23C 9/1307* (2013.01); *A23C 9/1425* (2013.01); *A23C 21/00* (2013.01); *A23J 1/205* (2013.01); *A23J 3/08* (2013.01); *A23L 2/66* (2013.01); *A23L 33/19* (2016.08); *A61K 8/986* (2013.01); *A61Q 19/00* (2013.01); *C07K 1/36* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 4,229,342 A | 10/1980 | Mirabel | |
| 4,691,011 A * | 9/1987 | Inagami | ............. A23C 19/0455 530/350 |
| 5,106,836 A | 4/1992 | Clemens et al. | |
| 2003/0096036 A1 * | 5/2003 | Bhaskar | ............... A23C 9/1422 426/36 |
| 2013/0011515 A1 | 1/2013 | Knights | |

FOREIGN PATENT DOCUMENTS

| | | |
|---|---|---|
| WO | 95/17830 | 7/1995 |
| WO | 2011/049991 | 4/2011 |

OTHER PUBLICATIONS

Int'l Search Report for PCT/IB2013/056610, four pages, mailed Nov. 15, 2013.
Written Opinion for PCT/IB2013/056610, three pages mailed Nov. 15, 2013.

* cited by examiner

*Primary Examiner* — Jeanette Lieb
(74) *Attorney, Agent, or Firm* — Nixon & Vanderhye PC

(57) ABSTRACT

The present invention relates to a method for the preparation of a concentrate of serum proteins with reduced lactose content from a sample of lactoserum, wherein said concentrate is characterized in that it comprises a concentration of 0.5 grams of lactose per kilogram of protein, the concentrate obtainable from said process and food products containing said concentrate.

14 Claims, No Drawings

METHOD FOR THE PREPARATION OF A SERUM PROTEIN CONCENTRATE

This application is the U.S. national phase of International Application No. PCT/IB2013/056610, filed 13 Aug. 2013, which designated the U.S. and claims priority to Italian Application No. RM2012A000412, filed 13 Aug. 2012; the entire contents of each of which are hereby incorporated by reference.

The present invention relates to a method for the preparation of a concentrate of proteins from a sample of lactoserum, wherein said concentrate is characterized in that it comprises a concentration of 0.5 grams of lactose per kilogram of proteins, the concentrate obtainable from said process, and products containing said concentrate.

STATE OF THE PRIOR ART

Whey (or also 'lactoserum') represents the liquid fraction of milk and contains a high percentage of lactose (between 50-75%) besides proteins, mineral salts, traces of lipids and lactose degradation products (lactic acid, glucose, galactose). Protein content of lactoserum ranges from about 8% to 14%; in particular, the presence of a mixture of proteins is possible, the main ones being albumin, -lactoglobulin, -lactoalbumin, seroalbumin, lactoferrin, immunoglobulin; essential amino acids (leucine, isoleucine, valine, threonine, tryptophan, lysine, phenylalanine, etc).

Various studies demonstrated how lactoserum proteins have beneficial effects on health. In particular, Wong et al. report how whey protein intake enhances the immune function thanks to the presence of immunoglobulins present therein (Wong & Watson 1995. Immunomodulatory effects of dietary whey proteins in mice. J Dairy Res. 62(2):359-68). Moreover, it has also been suggested how lactoserum protein intake may have a preventive effect against cancer development (Hakkak et al. Dietary whey protein protects against azoxymethane-induced colon tumors in male rats. Cancer Epidemiol. Biomarkers Prev. 10 (5): 555-8. PMID 11352868).

From a medical-scientific standpoint, specific interest was directed not only at lactoserum immunoglobulins, but also at lactoferrin, for which beneficial effects on health, such as improvement of immune, antimicrobial, antiviral and anti-cancer activity, have been described.

Lactoserum proteins are also known for their beneficial effect on skin.

Even though, as reported above, a set of beneficial effects are associated to lactoserum proteins, their intake or their use in general is limited by the fact that the lactoserum in which they are present is characterized by a high content of lactose sugar. In particular, in world population the intolerance to said molecule is widespread; it being mainly due to the subjects' inability to metabolize lactose owing to a deficit of the lactase enzyme. The incidence of said intolerance varies significantly from country to country, with a percent of about 22% of adult population in the United States, reaching up to about 70% in Southern Europe population.

The most common lactose intolerance-related symptomatology consists in essentially gastrointestinal disorders such as abdominal pains and cramps, feeling of swelling and tension at the intestinal level, increased peristalsis, flatulence, meteorism, diarrhoic bowel movements, etc.

The therapy par excellence in case of lactose intolerance is a diet regime with a reduced contribution of lactose-rich foods, therefore including lactoserum. However, such a therapy is particularly unsuitable in cases in which the intolerant subject is, e.g., a pediatric subject, a subject with malnutrition, with immune deficits, etc., in which lactoserum intake is fundamental to ensure adequate contribution of lactoserum proteins.

Therefore, in the state of the known art it is extremely felt the need to define techniques allowing to purify the mixture of serum proteins from lactoserum, minimizing the lactose content present therein and therefore ensuring the preservation of the composition of proteins, amino acids, etc., typical of whey.

SUMMARY OF THE INVENTION

The present description relates to a method for the preparation of a protein concentrate from lactoserum (also known as whey). In particular, such method comprises a series of operative steps whose end result is the obtainment of a concentrate of proteins from lactoserum (or also referred to as 'serum proteins') with extremely advantageous features.

In fact, the method described herein allows to reduce the content of lactose present in the lactoserum, concomitantly preserving its content in serum proteins, therefore, in other terms, without altering or modifying its peculiar composition in proteins, amino acids, mineral salts, etc.

In particular, the serum protein concentrate obtainable by the method described herein is characterized in that it has a concentration of 0.5 grams of lactose per kilogram of proteins. Moreover, proteins isolated from lactoserum according to what described below have a degree of purity of at least 96%.

Hence, the method object of the present description can be advantageously used for the preparation of concentrates of serum proteins from lactosera, intended, e.g., for subject with lactose intolerance or allergy, and/or in need of a significant contribution of serum proteins.

Moreover, the Authors of the present invention have also observed that the method described herein leads to a serum protein concentrate characterized by being free of unpleasant odours and tastes, typical instead of lactoserum proteins. Said further advantage in the final analysis determines, e.g., an easier use of the concentrate in subsequent stages, such as the preparation of products containing it, which by way of example but without being limited thereto, can be food, beauty, biotechnological products, etc.

Therefore, a first object of the present description is a method for the preparation of a concentrate of serum proteins with reduced lactose content from a sample of lactoserum, comprising the following steps:

a) concentrating said sample of lactoserum, thus obtaining a protein concentration of between about 150-300 grams/liter;

b) subjecting said lactoserum concentrate to at least one step of diafiltration;

c) diluting said diafiltered protein concentrate, thus obtaining a solution having a concentration of proteins in the range of about 50-90 grams/liter;

d) adding to said solution about 5-10 grams of a pyrogenic silica per liter of solution;

e) adding about 70-300 ml of ethanol 95% v/v, per kilogram of proteins, in said solution;

f) acidifying the pH of the solution obtained at e) up to a value of about 4.5-5;

g) heating the acidified solution at a temperature between about 55 and 70° C. for at least 20 minutes wherein said temperature is reached within about 30 minutes;

h) cooling the solution to a temperature between about 10 and 20° C.;

i) carrying out a separation of the cooled solution of proteins;

l) bringing the pH of the separate solution to a value of about 5.8-6.8;

m) subjecting the solution obtained at l) to at least one passage of microfiltration, thus obtaining a protein concentrate having a protein concentration of between about 100 and 300 grams/liter;

n) subjecting the protein concentrate to at least one step of diafiltration;

o) drying and/or freeze-drying said protein concentrate.

wherein said serum protein concentrate from lactoserum has a concentration of 0.5 grams of lactose per kilogram of proteins.

A second object of the present description is a protein concentrate from lactoserum (or serum proteins) comprising 0.5 grams of lactose per kilogram of protein.

Further objects of the present description are food, beauty or biotechnological products comprising the above lactoserum protein concentrate.

DETAILED DESCRIPTION OF THE INVENTION

The present invention relates to a method for the preparation of a concentrate of serum proteins with reduced lactose content from a sample of lactoserum. In other terms, the method described herein allows to isolate the mixture of proteins contained in the lactoserum reducing or eliminating the lactose present in the starting sample of whey.

In the present description, with the term "lactoserum" or "whey" it is meant the liquid fraction obtained from whole, skim or semi-skim milk after separation of the rennet.

In particular, the method object of the present description comprises the following operative steps:

a) concentrating said sample of lactoserum, thus obtaining a protein concentration of between about 150-300 grams/liter;

b) subjecting said lactoserum concentrate to at least one step of diafiltration;

c) diluting said diafiltered protein concentrate, thus obtaining a solution having a protein concentration in the range of about 50-90 grams/liter;

d) adding to said solution about 5-10 grams of a pyrogenic silica per liter of solution;

e) adding about 70-300 ml of ethanol 95% v/v, per kilogram of proteins, in said solution;

f) acidifying the pH of the solution obtained at e) up to a value of about 4.5-5.0;

g) heating the acidified solution at a temperature between about 55 and 70° C. for at least 20 minutes, wherein said temperature is reached within about 30 minutes;

h) cooling the solution to a temperature between about 10 and 20° C.;

i) carrying out a separation of the cooled solution of proteins;

l) bringing the pH of the separate solution to a value of about 5.8-6.8;

m) subjecting the solution obtained at l) to at least one passage of microfiltration, thus obtaining a protein concentrate having a protein concentration of between about 100 and 300 grams/liter;

n) subjecting the protein concentrate to at least one step of diafiltration;

o) drying and/or freeze-drying said concentrated protein.

wherein said serum protein concentrate from lactoserum has a concentration of 0.5 grams of lactose per kilogram of proteins.

The preparation of a concentrate of proteins according to the method described herein can be carried out from a sample of lactoserum which may comprise both sweet and acid lactoserum, or may contain only sweet lactoserum or only acid lactoserum. The lactoserum useful to the ends of the present invention may be of any origin; therefore, merely by way of a non-limiting example, such a lactoserum may be obtained from human, bovine, caprine milk, etc.

As indicated above, the method comprises a step of concentrating the starting sample of lactoserum, which may be carried out according to any one technique known to the technician in the field and suitable to that end. In a preferred embodiment of the present method, the concentrating step is carried out by ultrafiltration/s. For example, ultrafiltration, according to the above-indicated step a), is carried out by use of membranes having a cut-off of between about 10000 and 15000 daltons. Therefore, by way of illustration, membranes having a cut off of 10000, 11000, 12000, 13000, 14000 and/or 15000 may be used. To the ends of the obtainment of a lactoserum having a concentration of proteins of at least 150 grams/liter, one or more ultrafiltration steps and/or the use of one or more of the above-indicated membranes could be required.

The next stage, i.e. step b) of the above method, consists in reducing the maximum possible amount of lactose from the lactoserum concentrate according to what mentioned above. The total elimination or the partial reduction of the lactose content may be carried out, e.g., by at least one step of diafiltration. By "diafiltration" it is meant in general the separation of microsolutes from a solution of molecules, in this case proteins, by ultrafiltration carried out with continuous addition of solvent. For example, the diafiltration according to the present method may be carried out by using as solvent demineralized, distilled and/or osmotic water, but not saline solutions. Merely by way of example, three volumes of demineralized water may be used for each volume of lactoserum concentrate. In one embodiment of the present invention, the steps of diafiltration of the lactoserum concentrate are at least 3 and are carried out employing three volumes of demineralized water per each volume of lactoserum concentrate.

The diafiltered lactoserum, which owing to the above is characterized, compared to the starting lactoserum sample, by a reduced concentration of lactose, is then diluted by addition of a solvent, thus obtaining a solution of diafiltered lactoserum with a protein content of about 50-90 grams/liter. In particular, said solution may have a protein content of about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 grams/liter. In one embodiment of the invention, the solution of diafiltered lactoserum has a protein concentration of about 70 grams/liter. For instance, the dilution of the solution of diafiltered lactoserum is carried out by the use of demineralized water as solvent.

Step d) of the method described herein comprises adding to the diluted solution of lactoserum about 5-10 grams, e.g. 7 grams, of a pyrogenic silica per liter of solution.

Pyrogenic silica is a particular type of silica consisting in microscopic droplets of amorphous silica that agglomerate into tertiary particles with peculiar chemico-physical characteristics. Pyrogenic silica, usually present on the market in the form of a powder, is hydrophilic pyrogenic silica capable of fixing lipoproteins, residual fatty matter and/or macromolecules present in a given solution. At this time it is unnecessary to describe pyrogenic silica in detail, as it is well-known and widely used in various technical fields by those skilled in the art. Merely by way of example and without limitative purposes to the ends of the present invention, the pyrogenic silica may be of Aerosil® type, e.g. Aerosil® 380 and/or Aerosil® 200.

Subsequently to the adding of the above silica, about 70-300 ml of ethanol 95% v/v, per kilogram of proteins, are added to the solution. For instance, the amount of ethanol added is of about 120 ml per kilogram of proteins and even more; for instance, the ethanol is of food grade.

Thereafter, in accordance with step f) of the method described herein, the pH of the solution is brought to a value of about 4.5 to 5.0, e.g. by use of HCl. Solution pH at the end of step f) could be a pH of 4.6, 4.7, 4.8, 4.9, 5.0; e.g., the pH will have a value of 4.6.

The acid solution thus obtained is then heated to a temperature between 55 and 70° C. for at least 20 minutes. In particular, said heating temperature may be of 55, 56, 57, 58, 59, 60, 61, 62, 63, 64, 65, 66, 67, 68, 69, 70° C., e.g. of 66° C. To the ends of the present invention, the heretodescribed heating, in actual fact consisting in the temperature increase from the initial temperature of the starting sample of lactoserum to the above-indicated temperature of interest, should take place in an interval of at least 30 minutes. In particular, the Inventors of the present method observed that a quicker heating of the solution determines a loss in the yield of purified serum proteins, whereas a slower heating thereof determines a non-satisfactory purification of serum proteins, since proteins not of interest, like, e.g., casein, are not eliminated.

Thereafter, the heated solution is cooled to a lower temperature, between 10 and 20° C., therefore to a temperature of 10, 11, 12, 13, 14, 15, 16, 17, 18, 19 or 20° C.

Said cooled solution is subjected to separation in order to isolate the fraction containing the serum proteins. Such step i) of the method described herein may be carried out according to any one separation/purification technique deemed by the technician in the field suitable to allow the of the protein component from the above solution. Merely by way of example, the separation may be continuous by utilizing Alfa laval or Westfalia separators.

The pH of the separate solution, containing the serum proteins, is then brought to a value of between 5.8 and 6.8, e.g. by use of NaOH. The solution pH at the end of such step l) could be a pH of 5.8, 5.9, 6.0, 6.1, 6.2, 6.3, 6.4, 6.5, 6.6, 6.7 or 6.8; e.g., the pH will have a value of 6.4.

Then, in accordance to step m) of the method object of the present description, the solution of serum proteins is subjected to at least one passage of microfiltration, thus obtaining a protein concentrate having a protein concentration of between about 100 and 300 grams/liter. In one embodiment of the present method, microfiltration is carried out with membranes having a cut-off of about 12 microns or 0.6 microns. In particular, at least one first passage of microfiltration can be carried out by using membranes with a cut-off of 12 microns, followed by one or more passages of microfiltration using membranes with a cut-off of 6 microns. For instance, the microfiltration membranes to be used in the method described herein are organic and/or ceramic membranes.

Thereafter, the microfiltered solution of serum proteins is subjected to at least one step of diafiltration that may be carried out analogously to what already described hereto for step b) of the method of the present description.

Finally, the microfiltered and diafiltered solution of lactoserum proteins is dried and/or freeze-dried, thereby obtaining a concentrate of serum proteins from lactoserum.

The concentrate of proteins from lactoserum or of serum proteins obtainable by the above-described method is characterized, in particular, by having a concentration of 0.5 grams of lactose per kilogram of proteins. Moreover, the method leads to a concentrate of serum proteins wherein the purity of the proteins contained therein is of at least 96%.

In addition, the protein concentrate obtainable according to what disclosed herein is also characterized by being free of unpleasant odours and/or tastes typical of lactoserum proteins.

As already indicated, the chemico-physical characteristics of said concentrate make it particularly advantageous under conditions in which it is necessary that the content of lactose present therein be reduced to a minimum or, e.g., absent, as in the case in which its intended end use involves subjects intolerant and/or allergic to lactose. According to what has been mentioned hereto, object of the present invention are also products comprising the above-described protein concentrate. In particular, such products can be intended for any field of the art, such as, for instance and without being limited thereto, products of the food, cosmetic, biotechnological field. Merely by way of example, the food products can be foods intended for nourishment of babies, ill subjects, children, elderly persons, or simply of persons following a particular diet regime, for instance, soups, yoghurt, milk, fruit juices, desserts, etc. In the cosmetic field, instead, the concentrate object of the present invention can be comprised in moisturizing products, or in general in products enabling to nourish skin cells. Moreover, in the biotechnological field, the concentrate of serum proteins may be, e.g., used as element to be introduced in culture media for mammalian cells or for microorganisms intended, e.g., for production of recombinant proteins.

Said products will have a concentration per kilogram of proteins equal to that of the concentrate of the present description.

In the products according to the present description the serum proteins will be those comprised in the concentrate according to the present description, and therefore the product itself will have a lactose concentration equal to 0.5 grams of lactose per kilogram of proteins of lactoserum.

In case of products like milk or yoghurt comprising the concentrate of the present description, in order to maintain the absence of lactose and increase the concentration of serum proteins, thereby obtaining a product with a greater protein concentration, delactosed milk could be used as starting product to which the concentrate of the present description will be added.

EXAMPLES

Example 1

Enrichment of food products with the concentrate of lactoserum proteins.

The food products comprising the concentrate of serum proteins can be prepared as follows.

Soups: between 10 and 15 g of concentrate for a soup portion of between 150 and 250 ml;
Milk: between 5 and 10 g of serum proteins for a milk portion of between 150 and 250 ml;
Yoghurt: between 5 and 10 g of concentrate for a yoghurt portion of between 100 and 250 ml;

Fruit juice: between 5 and 10 g of concentrate for a portion of between 100 and 1000 ml;

Dessert: between 5 and 10 g of concentrate for a dessert portion of between 100 and 250 ml;

The invention claimed is:

1. A method for the preparation of a concentrate of serum proteins with reduced lactose content from a sample of lactoserum, comprising the following steps:
   a) concentrating said sample of lactoserum, thus obtaining a lactoserum concentrate having a protein concentration of between about 150-300 grams/liter;
   b) subjecting said lactoserum concentrate to at least one step of diafiltration, thus obtaining a diafiltered protein concentrate;
   c) diluting said diafiltered protein concentrate, thus obtaining a solution having a protein concentration in the range of about 50-90 grams/liter, thus obtaining a diluted solution;
   d) adding to said diluted solution about 5-10 grams of a pyrogenic silica per liter of diluted solution;
   e) adding about 70-300 ml of ethanol 95% v/v per kilogram of proteins to the solution obtained at step d);
   f) acidifying the pH of the solution obtained at step e) up to a value of about 4.5-5.0, thus obtaining an acidified solution;
   g) heating the acidified solution at a temperature between about 55° C. and 70° C. for at least 20 minutes, wherein said temperature is reached within about 30 minutes;
   h) cooling the solution heated at step g) to a temperature between about 10° C. and 20° C., thus obtaining a cooled solution;
   i) carrying out a separation of the cooled solution of proteins, thus obtaining a separate solution;
   l) bringing the pH of the separate solution to a value of about 5.8-6.8;
   m) subjecting the solution obtained at step l) to at least one passage of microfiltration, thus obtaining a microfiltered protein concentrate having a protein concentration of between about 100 and 300 grams/liter;
   n) subjecting the microfiltered protein concentrate to at least one step of diafiltration, thus obtaining a twice-filtered protein concentrate; and
   o) drying and/or freeze-drying said twice-filtered protein concentrate, thus obtaining a serum protein concentrate from lactoserum;

wherein said serum protein concentrate from lactoserum has a concentration of ≤0.5 grams of lactose per kilogram of proteins.

2. The method according to claim 1, wherein said sample of lactoserum comprises sweet and/or acid lactoserum.

3. The method according to claim 1, wherein the concentrating at step a) is carried out by ultrafiltration.

4. The method according to claim 3, wherein said ultrafiltration is carried out with a membrane having a cut-off of between about 5000-15000 daltons.

5. The method according to claim 1, wherein said at least one diafiltration step at b) and n) are at least three.

6. The method according to claim 1, wherein said at one step of diafiltration at b) is carried out using as solvent demineralized water and/or deionized water and/or an osmotic solution.

7. The method according to claim 6, wherein said diafiltration is performed using 3 volumes of said solvent per each volume of the lactoserum concentrate.

8. The method according to claim 1, wherein said step d) is carried out by adding about 7 grams of pyrogenic silica per liter of said diluted solution.

9. The method according to claim 1, wherein said step e) is carried out by adding about 100-150 ml of ethanol per kilogram of protein in said solution obtained in step d).

10. The method according to claim 1, wherein said step g) is carried out at a temperature of about 66° C.

11. The method according to claim 1, wherein said at least one passage of microfiltration at step m) is carried out using a membrane with a cut-off of about 12 microns or 0.6 microns.

12. The method according to claim 1, wherein said proteins are at least 96% pure.

13. A lactoserum protein concentrate obtained by the method according to claim 1, wherein said lactoserum protein concentrate comprises ≤0.5 grams of lactose per kilogram of protein.

14. A lactoserum protein concentrate obtained by the method according to claim 1, wherein said proteins are at least 96% pure.

* * * * *